United States Patent
Goux et al.

[11] Patent Number: 6,110,384
[45] Date of Patent: Aug. 29, 2000

[54] METHOD OF DETERMINING A PARAMETER INDICATIVE OF THE PROGRESS OF AN EXTRACORPOREAL BLOOD TREATMENT

[75] Inventors: Nicolas Goux, Craponne, France; Jan Sternby, Lund, Sweden

[73] Assignees: Gambro, AB, Lund, Sweden; Hospal Industrie, Meyzieu, France

[21] Appl. No.: 09/152,071

[22] Filed: Sep. 11, 1998

[30] Foreign Application Priority Data

Dec. 9, 1997 [FR] France ................................ 97 15818

[51] Int. Cl.⁷ .................................................. B01D 61/54
[52] U.S. Cl. .................. 210/739; 210/96.2; 210/645; 210/646; 210/746; 604/4.01
[58] Field of Search ................... 210/85, 96.2, 321.7, 210/646, 647, 739, 929, 645, 746; 604/4, 5, 4.01, 5.01, 6.01, 6.09; 364/528.08

[56] References Cited

U.S. PATENT DOCUMENTS

| | | | |
|---|---|---|---|
| 5,024,756 | 6/1991 | Sternby | 210/93 |
| 5,100,554 | 3/1992 | Polaschegg | 210/647 |
| 5,507,723 | 4/1996 | Keshaviah | 604/5 |
| 5,567,320 | 10/1996 | Goux et al. | 210/739 |
| 5,662,806 | 9/1997 | Keshaviah et al. | 210/739 |
| 5,725,773 | 3/1998 | Polaschegg | 210/646 |
| 5,900,726 | 5/1999 | Brugger et al. | 210/646 |

FOREIGN PATENT DOCUMENTS

| | | |
|---|---|---|
| 0 428 927 | 5/1991 | European Pat. Off. . |
| 0 547 025 | 6/1993 | European Pat. Off. . |
| 0 658 352 | 6/1995 | European Pat. Off. . |
| WO 95/32010 | 11/1995 | WIPO . |
| WO 98/32476 | 7/1998 | WIPO . |

*Primary Examiner*—Joseph W. Drodge
*Attorney, Agent, or Firm*—Finnegan, Henderson, Farabow, Garrett & Dunner, L.L.P.

[57] ABSTRACT

A method is disclosed for determining a parameter (D, K, Kt/v, Cbin) indicative of the effectiveness of an extracorporeal blood treatment carried out using a membrane exchanger. The method includes the steps of flowing through the exchanger a treatment liquid having a concentration characteristic (Cd) and of varying the value of the characteristic (Cd) upstream of the exchanger for a time at the end of which the characteristic (Cd) is returned to a nominal value. A plurality of values adopted by the characteristic (Cd) downstream of the exchanger in response to the upstream variation is measured and stored in memory. The area (Sout) of a downstream perturbation region is determined, which is bounded by a baseline and a curve representing the variation of the measured values with respect to time. Then, the parameter (D, K, Kt/v, Cbin) indicative of the effectiveness of the treatment is calculated using the area (Sin) beneath the upstream curve and an area beneath an upstream curve.

20 Claims, 3 Drawing Sheets

METHOD OF DETERMINING A PARAMETER INDICATIVE OF THE PROGRESS OF AN EXTRACORPOREAL BLOOD TREATMENT

BACKGROUND OF THE INVENTION

1. Field of the Invention

The invention relates to a method of determining a parameter indicative of the progress of an extracorporeal blood treatment, in particular a purification treatment whose purpose is to alleviate renal insufficiency, such as haemodialysis or haemodiafiltration.

2. Description of the Related Art

It will be recalled that haemodialysis consists in making a patient's blood and a treatment liquid approximately isotonic with blood, flow, one on each side of the semipermeable membrane of an exchanger, so that, during the diffusive transfer which is established across the membrane in the case of substances having different concentrations on either side of the membrane, the impurities in the blood (urea, creatinine, etc.) migrate from the blood into the treatment liquid. The electrolyte concentration of the treatment liquid is also generally chosen so as to correct for the electrolyte concentration of the patients blood.

In treatment by haemodiafiltration, a convective transfer by ultrafiltration, resulting from a positive pressure difference created between the blood side and the treatment-liquid side of the membrane, is added to the diffusive transfer obtained by dialysis.

It is of the utmost interest to be able to determine, throughout a treatment session, one or more parameters indicative of the progress of the treatment so as to be able, where appropriate, to modify the treatment conditions that were fixed initially for the purpose of a defined therapeutic objective.

The parameters, the knowledge of which makes it possible to follow the progress of the treatment, i.e. also to assess the suitability of the initially fixed treatment conditions to the therapeutic objective, are, in particular, the concentration in the blood of a given solute (for example, sodium) or the actual dialysance or the actual clearance of the exchanger for such and such a solute (the dialysance and the clearance representing the purification efficiency of the exchanger) or the dialysis dose administered after a treatment time t, which, according to the work of Sargent and Gotch, may be likened to the dimensionless ratio Kt/V, where K is the actual clearance for urea, t the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp, 526–34).

These parameters all have the same problem in respect of their determination, which is of requiring precise knowledge about a physical or chemical characteristic of the blood, whereas this characteristic cannot in practice be obtained by direct measurement on a specimen for therapeutic, prophylactic and financial reasons: firstly, it is out of the question to take, from a patient who is often anaemic, multiple specimens which would be necessary in order to monitor the effectiveness of the treatment during its execution; furthermore, given the risks associated with handling specimens of blood which may possibly be contaminated, the general tendency is to avoid such handling operations; finally, laboratory analysis of a specimen of blood is both expensive and relatively lengthy, this being incompatible with the desired objective.

Document EP 0,658,352 describes a method for the in vivo determination of the haemodlalysis parameters which does not require taking measurements on the blood. This method, the implementation of which requires means for controlling the ion concentration in the treatment liquid and means for measuring the sodium concentration in the treatment liquid or its conductivity, comprises the steps of:

making at least a first (d1) and a second (d2) treatment liquid, having a characteristic (Cd) associated with at least one of the parameters (Cb, D, K, Kt,V) indicative of the treatment, flow in succession through the exchanger, the value of the characteristic in the first liquid (d1) upstream of the exchanger being different from the value of the characteristic (Cd) in the second liquid (d2) upstream of the exchanger;

measuring, in each of the first (d1) and second (d2) treatment liquids, two values (Cd1in, Cd1out; Cd2in, Cd2out) of the characteristic (Cd), respectively upstream and downstream of the exchanger;

making a third treatment liquid (d3) flow through the exchanger while the characteristic (Cd) of the second liquid (d2) has not achieved a stable value downstream of the exchanger, the value of the characteristic (Cd) in the third liquid (d3) upstream of the exchanger being different from the value of the characteristic (Cd) in the second liquid (d2) upstream of the exchanger;

measuring two values (Cd3in, Cd3out) of the characteristic (Cd) in the third liquid (d3) respectively upstream and downstream of the exchanger; and calculating at least one value of at least one parameter (Cb, D, K, Kt/V) indicative of the progress of the treatment from the measured values of the characteristic (Cd) in the first (d1), second (d2) and third (d3) treatment liquids.

SUMMARY OF A FEW ASPECTS OF THE INVENTION

An object of the invention is to design a method of determining a parameter indicative of the progress of an extracorporeal blood treatment which is at least as reliable as the abovementioned method, i.e. by virtue of which the parameters indicative of the progress of the treatment can be precisely determined, frequently, and without the patient having to be durably subjected to treatment conditions different from the prescribed conditions.

In order to achieve this object, the invention provides a method of determining a parameter (D, K, Kt/v, Cbin) indicative of the effectiveness of an extracorporeal treatment of blood, consisting in making a patient's blood and a treatment liquid flow one on each side of the semipermeable membrane of a membrane exchanger, the method including the steps of:

making a treatment liquid flow through the exchanger, this treatment liquid having a characteristic (Cd) which has an approximately constant nominal value (Cd0in) upstream of the exchanger;

varying the value of the characteristic (Cd) upstream of the exchanger for a time tc−ta, at the end of which the characteristic (Cd) is returned to its nominal value (Cd0in) upstream of the exchanger;

measuring and storing in memory a plurality of values adopted by the characteristic (Cd) of the treatment liquid downstream of the exchanger in response to the variation in the value of this characteristic (Cd) caused upstream of the exchanger;

determining the area (Sout) of a downstream perturbation region bounded by:

a baseline passing through two values given by the characteristic (Cd) at two times flanking the perturbation, at which times the characteristic (Cd) is not, or alternatively is no longer, influenced by the perturbation, and a curve representing the variation with respect to time of the characteristic (Cd), established from the values of the characteristic (Cd) which are measured downstream of the exchanger between two times t1 and t3 flanking the perturbation, at which times the characteristic (Cd) is not, or alternatively is no longer, influenced by the perturbation; and calculating the parameter (D, K, Kt/v, Cbin) indicative of the effectiveness of a treatment from the area (Sout) of the downstream perturbation region and from the area (Sin) of an upstream perturbation region bounded by:

a baseline consisting of the nominal value (Cd0in) of the characteristic (Cd), and a curve representing the variation with respect to time, over the period tc–ta, of the characteristic (Cd) upstream of the exchanger.

This method has the advantage of allowing precise determination of the parameters indicative of the progress of the treatment from measurements taken at close time intervals. Consequently, the patient is exposed only for a very short time to a treatment liquid different from the prescribed treatment liquid (for example, one which is too rich or too poor in sodium) and the method can be employed as often as necessary for suitable monitoring of the treatment session. Moreover, insofar as the quantities involved in the calculations carried out according to this method are areas and not isolated values, this method is insensitive to all kinds of incidents which may occur during the measuring of an isolated value and which may falsify the subsequent calculations by using an erratic value.

According to one characteristic of the invention, the step of varying the value of the characteristic (Cd) of the treatment liquid upstream of the exchanger comprises the steps of:

setting the characteristic, over a first defined time interval, to a first defined set value above (or below) the nominal value (Cd0in), and setting the characteristic, over a second time interval, to a second set value below (or above) the nominal value (Cd0in).

Preferably, the duration of the second time interval as well as the absolute value of the second set value are chosen so that the characteristic (Cd) resumes its initial value (Cd0out) downstream of the exchanger in a minimum amount of time.

According to another characteristic of the invention, the method furthermore comprises, prior to the step of varying the value of the characteristic (Cd), the steps of:

giving the parameters of the variation a defined value, so that the area of the upstream perturbation region Sin is constant when the predetermined parameters of the variation are complied with;

determining and storing in memory the area of the upstream perturbation region Sin for a variation having the fixed parameters.

When the characteristic subjected to variation is the concentration in the treatment liquid of a substance present in both the treatment liquid and the blood, it is possible according to the invention, to calculate the dialysance D of the exchanger for this substance and/or the concentration Obin of the substance in the patient's blood upstream of the exchanger by means of the formulae:

$$D = (Qd + Quf) \times (1 - Sout/Sin)$$

$$Cbin = \left( \frac{Cd0in \times Sout/Sin + Cd0out}{(1 - Sout/Sin)} \right)$$

Other characteristics and advantages of the invention will appear on reading the description which follows.

BRIEF DESCRIPTION OF THE DRAWINGS

Reference will be made to the drawings, in which.

DESCRIPTION OF THE PREFERRED EMBODIMENTS

Figure 1:
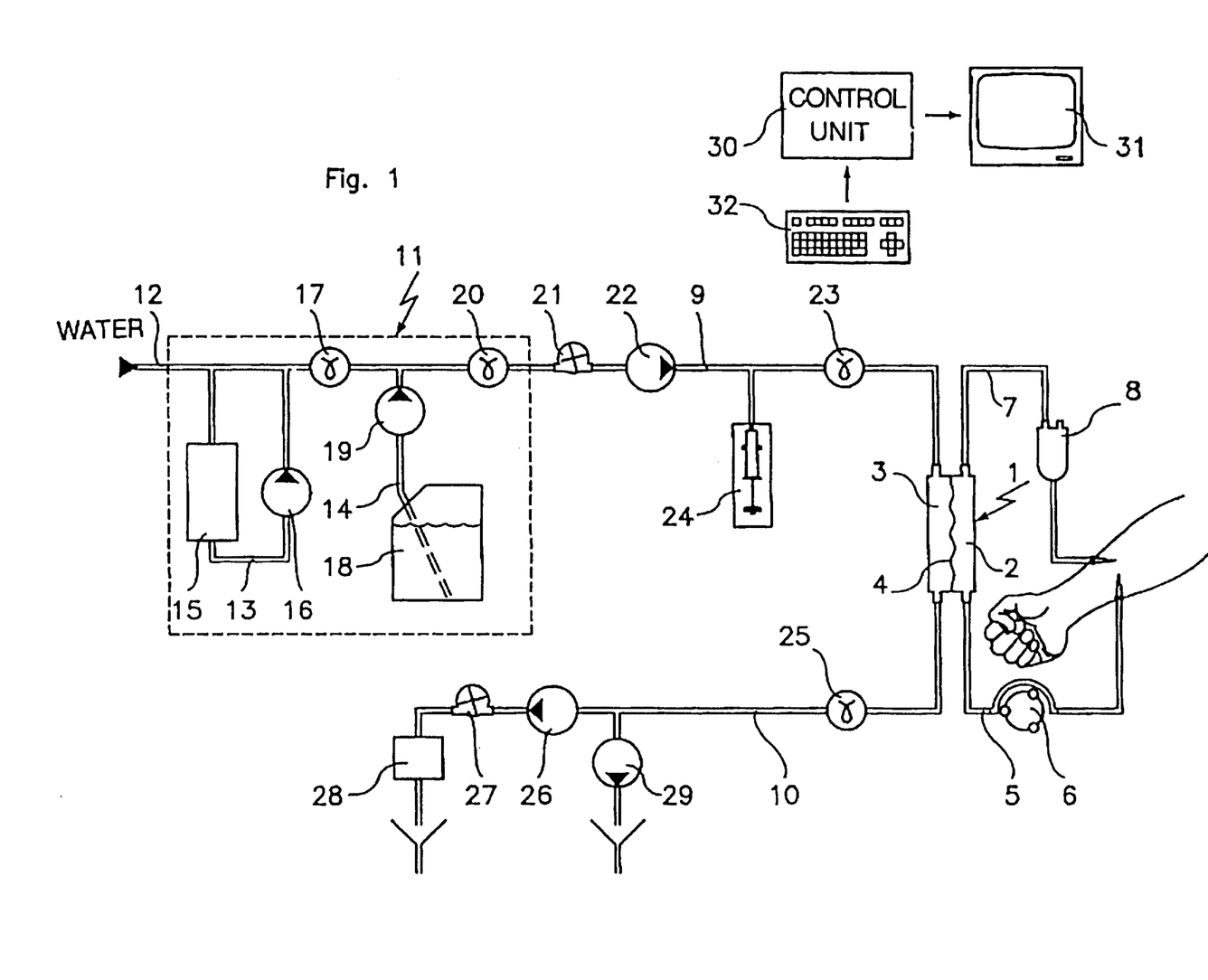
FIG. 1 is a partial diagrammatic representation of a haemodialysis/haemodiafiltration system suitable for implementing the method according to the invention.

The haemodialysis system shown in FIG. 1 comprises a haemodialyser 1 having two compartments 2, 3 separated by a semipermeable membrane 4. A first compartment 2 has an input connected to a blood removal line 5, in which a circulating pump 6 is placed, and an output connected to a blood return line 7, in which a bubble trap 8 is placed.

The second compartment 3 of the haemodialyser 1 has an input connected to a line 9 for supplying fresh dialysis liquid and an output connected to a line 10 for discharging spent liquid (dialysis liquid and ultrafiltrate).

The supply line 9 connects the haemodialyser 1 to a dialysis. liquid preparation device 11 comprising a main line 12, the upstream end of which is intended to be connected to a supply of running water. A first secondary line 13 and a second secondary line 14 are connected to this main line 12. The first secondary line 13, which is looped back onto the main line 12, is provided with coupling means for fitting a cartridge 15 containing sodium bicarbonate in the form of granules. It is furthermore equipped with a pump 16 for metering bicarbonate into the dialysis liquid, this pump being placed downstream of the cartridge 15. The pump 16 is driven as a function of the comparison between 1) a first conductivity set value for the solution forming at the junction of the main line 12 and the secondary line 13 and 2) the value of the conductivity of this mixture, measured by means of a first conductivity probe 17 placed in the main line 12 immediately downstream of the junction between the main line 12 and the first secondary line 13.

The free end of the second secondary line 14 is intended to be immersed in a container 18 for a concentrated saline solution containing sodium chloride, calcium chloride, magnesium chloride and potassium chloride, as well as acetic acid. The second line 14 is equipped with a pump 19 for metering sodium into the dialysis liquid, this pump being driven depending on the comparison between 1) a second conductivity set value for the solution forming at the junction of the main line 12 and the second secondary line 14 and 2) the value of the conductivity of this solution measured by means of a second conductivity probe 20 placed in the main line 12 immediately downstream of the junction between the main line 12 and the secondary line 14.

The supply line 9 forms the extension of the main line 12 of the dialysis-liquid preparation device 11. Placed in this supply line are, in the direction of flow of the liquid, a first flow meter 21, a first circulating pump 22 and a third conductivity probe 23. Injection means 24 used to inject a precise volume of liquid, at a precise flow rate, such as a syringe fitted in a syringe driver, are connected to the supply line 9 between the first circulating pump 21 and the third conductivity probe 2.

The downstream end of the spent-liquid discharge line 10 is intended to be connected to the drain. Placed in this line are, in the direction of flow of the liquid, a third conductivity probe 25, a second circulating pump 26, a second flow meter 27 and a device 28 for measuring the urea. An extraction pump 29 is connected to the discharge line 10, upstream of the second circulating pump 26.

The haemodialysis system shown in FIG. 1 also comprises a computing and control unit 30. This unit is connected to a screen 31 and to a keyboard 32 via which the user inputs various set values to it, namely flow rate set values (blood flow rate Qb, dialysis liquid flow rate Qd), conductivity set values used for preparation of the dialysis liquid, a treatment duration set value T and a weight loss set value WL. Moreover, the computing and control unit 30 receives information sent out by the measurement devices of the system, such as the flow meters 21, 27, the conductivity probes 17, 20, 23, 25, and the urea-measuring device 28. It controls, depending on the instructions received and on programmed algorithms and operating modes, the devices for driving the system, such as the pumps 6, 16, 19, 22, 26, 29.

The haemodialysis system which has just been described operates in the following manner.

After the extracorporeal blood circuit has been flushed and filled with sterile saline solution, it is connected to the patient and the blood pump 6 is switched on at a predetermined flow rate Qb, for example 200 m/min.

Simultaneously, the pumps 16 and 19 of the dialysis-liquid preparation device 11, the dialysis-liquid circulating pumps 22, 26 and the extraction pump 29 are switched on. The flow rate of the metering pumps 16, 19 is set by means of the conductivity probes 17, 20 so that the dialysis liquid has the desired bicarbonate and sodium concentrations. The flow rate Qd of the circulating pump 22 placed in the supply line 9 is set to a fixed value (500 ml/min, for example) while the flow rate of the circulating pump 26 placed in the discharge line 10 is permanently adjusted so that the flow rate measured by the second flow meter 27 is equal to the flow rate measured by the first flow meter 21. The output of the extraction pump 29 is set so as to be equal to the rate of weight loss (calculated from the weight WL which the patient is prescribed to lose and from the duration T of the treatment session) to which is possibly added the flow rate of a liquid infused into the patient.

In accordance with the invention, the effectiveness of the treatment administered to the patient by means of the system which has just been described is determined either at any moment according to the physician's choice or at programmed time intervals, by means of the following method.

Defined in a general way, the method of determining a parameter indicative of the effectiveness of the treatment according to the invention consists 1) in creating a perturbation in the exchange conditions established within the haemodialyser 1 by modifying a stable characteristic of the dialysis liquid for a short space of time (two to three minutes, for example, while a haemodialysis session lasts approximately four hours), 2) in determining a quantity indicative of the variation imposed on the characteristic of the dialysis liquid upstream of the haemodialyser, 3) in determining a quantity indicative of the variation of the characteristic, as it appears downstream of the haemodialyser 1, deformed by the exchanges taking place, in respect of this characteristic, in the haemodialyser 1 and 4) in computing a parameter indicative of the effectiveness of the treatment administered based on the quantity indicative of the variation in the characteristic upstream of the haemodialyser and on the quantity indicative of the variation in the characteristic downstream of the haemodialyser.

In detail, the steps of the method may be carried out in the following manner.

1—Creation of a perturbation in the exchange conditions established in the haemodialyser 1.

The concentration of a substance set, during ordinary operation of the system, to a stable value Cd0in in the dialysis liquid, is modified.

This substance may be sodium, in which case the variation in the sodium concentration in the dialysis liquid may be obtained either by varying the output of the sodium-metering pump 19, according to a programmed sequence, or by injecting, into the fresh dialysis liquid, by means of the syringe driver 24, a defined volume of a sodium chloride solution having a concentration greater than or less than the sodium concentration Cd0in prescribed for the dialysis liquid.

The variation in the sodium concentration of the dialysis liquid, i.e. therefore the variation in its conductivity, may consist of a momentary increase in the concentration, of a momentary decrease in the concentration or of a momentary increase/decrease sequence in the concentration, or vice versa, (such a sequence can only be implemented by means of the sodium metering pump 19, or it is necessary to use two syringe drivers containing sodium chloride solutions whose concentration is respectively greater than and less than the concentration of the dialysis liquid Cd0in).

Although this step in the method can be implemented by injecting, into the supply line 9, an undefined volume, at a flow rate which is varied to a greater or lesser extent, of a sodium chloride solution whose sodium concentration is not precisely known, it is advantageous to programme the parameters of the variation in the control unit 30. If the variation is caused by the sodium metering pump 19, the variation will then be defined by a specific output of the pump (greater than, or less than, or greater than and then less than, or vice versa, the nominal output of the pump) and the time interval (or intervals) during which the pump 19 will be driven at this specific output (or these specific outputs). If the variation is caused by the syringe driver 24, a calibrated variation will be defined by the sodium concentration of this solution, by the volume of solution injected and by the rate of injection.

According to an alternative way of implementing the method of the invention, instead of varying, in the dialysis liquid, the concentration of a substance present in the dialysis liquid, the concentration of a substance present in the blood and absent from the dialysis liquid, such as urea, is varied. The syringe driver 24 is then used to inject, into the dialysis liquid, a solution isotonic with the blood and containing urea.

As will become apparent later, the method according to the invention delivers information which is all the more reliable because it occurs during a very stable stage of operation of the haemodialysis system, in which all the operating parameters of the system, apart from the characteristic of the dialysis liquid which has been chosen to vary, remain approximately constant (in particular, the blood and dialysis liquid flow rates). It is therefore advantageous to ensure that the method is implemented briefly, i.e. also to shape the variation induced in the fresh dialysis liquid in such a way that the conductivity of the dialysis liquid downstream of the haemodialyser 1 assumes the initial value Cd0out, which it had before the perturbation, as rapidly as possible.

To this end, it is advantageous to programme a variation in the conductivity which includes a first step of predetermined magnitude and duration (for example +1 mS/cm with respect to the nominal conductivity Cd0in, for 60 seconds) followed by a step in the opposite direction of predetermined magnitude (for example −1 mS/cm with respect to the nominal conductivity Cd0in). The duration of the second step may be fixed at a predetermined value (for example, 30 seconds) which will have been chosen empirically based on practical tests on various types of haemodialyser, for dialysis-liquid and blood flow rates lying within the ranges of flow rates usually used in haemodialysis. The duration of the counter-step may also be adjusted by the control unit 30 depending on the conductivity of the spent liquid measured by the conductivity probe 25 placed in the discharge line 10. In a more sophisticated alternative version of the method, the control unit 30 adjusts, depending on the change in conductivity downstream of the haemodialyser 1 resulting from the step, both the magnitude and the duration of the counter-step so that the conductivity measured by the probe 25 reverts as rapidly as possible after the perturbation to the initial stable conductivity value Cd0out.

2—Determination of a quantity indicative of the variation imposed on the chosen characteristic of the dialysis liquid.

It will be assumed below that, by way of example, this characteristic is the sodium concentration in the dialysis liquid, i.e. also its conductivity. In accordance with the invention, the quantity chosen is the area Sin of a region called the "upstream perturbation region", which is defined as follows, With the haemodialysis system operating under stable exchange conditions with regard to the sodium concentration, with the conductivity Cd0in of the fresh dialysis liquid, as measured by the probe 23, being equal to the prescribed conductivity (or nominal conductivity) and with the conductivity Cd0out of the spent dialysis liquid, as measured by the probe 25, being substantially constant, the control unit 30 causes, at a predetermined time, a variation in the conductivity of the dialysis liquid by driving the pump 19 or the syringe driver 24 in the manner described above. The conductivity probe 23 measures the variation in the conductivity of the fresh dialysis liquid continuously, while the control unit 30 samples and stores in memory, at predetermined time intervals Δt, a plurality of conductivity values Cdiin until the conductivity has resumed its nominal value Cd0in.

Figure 2:
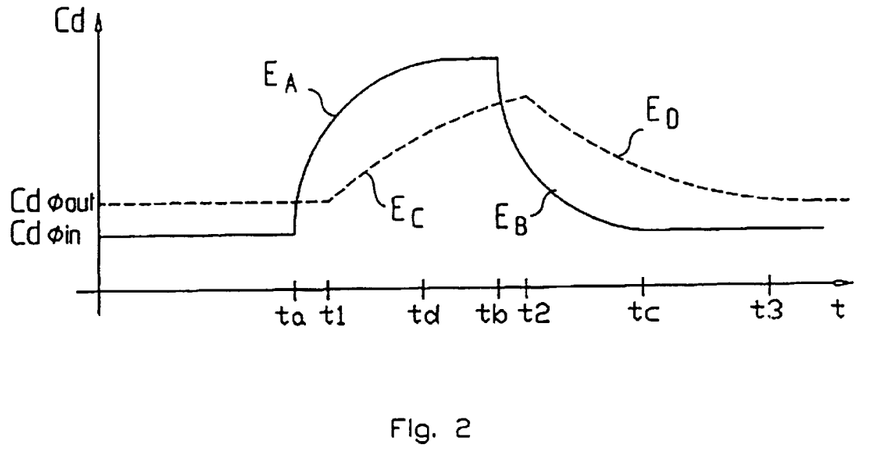
FIG. 2 is a diagram showing the variation in the conductivity of the treatment liquid as a function of time during implementation of the method according to the invention.

FIG. 2 shows diagrammatically the variation as a function of time in the conductivity of a dialysis liquid in response to an increase in the sodium concentration of the dialysis liquid during a predetermined time tb−ta (conductivity step). The curve plotted with a solid line represents the conductivity upstream of the haemodialyser 1, as measured by the conductivity probe 23, and the curve plotted with a broken line represents the conductivity downstream of the haemodialyser 1, as measured by the conductivity probe 25.

When the conductivity of the fresh dialysis liquid has resumed its nominal value Cd0in, the control unit 30 computes the area Sin of the upstream perturbation region, which is bounded by:

a baseline consisting of the nominal value of the conductivity (Cd0in) of the fresh dialysis liquid, and a curve representing the variation with respect to time in the conductivity over the duration of the perturbation tc−ta, this curve being established from the values Cdiin measured by the probe 23 and sampled and stored in memory by the control unit 30.

According to one embodiment of the invention, the calculation of the area Sin of the upstream perturbation region consists in summing a plurality of n elementary areas, each elementary area being equal to the product of the sampling time interval Δt and each sampled value Gdiin decreased by the nominal conductivity value Cd0in.

$$Sin = \Delta t \times \sum_{0}^{n} [Cdiin - Cd0in]$$

According to another embodiment, the control unit 30 calculates the area Sin of the upstream perturbation region according to the following steps:

determination of an equation of the curve representing the variation, as a function of time, in the sampled values Cdiin of the conductivity;

calculation of the integral of this equation between the start and end of the variation in the conductivity; and calculation of the area Sin of the upstream perturbation region, by subtracting from the calculated integral an area equal to the product of the duration of the perturbation tc−ta and the nominal value of the conductivity Cd0in.

The method for determining the equation of the curve must, of course, be chosen depending on the shape of the variation. By way of example, when the variation in the conductivity results from the increase (or decrease) in the nominal conductivity Cd0in by a given amount during a given period of time, followed by a return to the nominal conductivity (conductivity step), the curve representing the variation, as a function of time, in the sampled values Cdiin is composed of two exponential portions, as shown clearly in FIG. 2. The equation of each exponential can be calculated even before it reaches, in respect of the first exponential $E_A$, the junction point, occurring at time tb, of the exponential $E_A$ with the second exponential $E_B$ and, in respect of the exponential $E_B$ even before the return of the conductivity to its nominal value Cd0in, which occurs at time tc.

Taking the example of the first exponential $E_A$, its equation between ta and tb, $yA = c + a \times e^{-bt}$ is calculated from 3n consecutive conductivity values Cbiin sampled between time ta and time td in the following manner:

the three following sums are calculated:

$$S1 = \sum_{1}^{n} Cdiin \quad S2 = \sum_{n+1}^{2n} Cdiin \quad S3 = \sum_{2n+1}^{3n} Cdiin$$

the time constant b is calculated from the following equation:

$$1/b = n \times \Delta t / \ln \frac{(S1-S2)}{(S2-S3)}$$

the asymptotic value c is calculated from the following equation:

$$c = 1/n \times \frac{S1 \times S3 - S2^2}{S1 + S3 - 2 \times S2}$$

knowing c, the coefficient a is immediately obtained:

$$a = Cd0in - c$$

The equation $yB = c' + a' \times e^{-b't}$ of the second exponential $E_B$ between tb and tc is calculated in the same way.

The area Sin of the upstream perturbation region bounded between the exponentials $E_A$ and $E_B$ and the baseline consisting of the nominal value of the conductivity Cd0in may be calculated using the formula:

$$Sin = \int_{ta}^{tb}(c + a \times e^{-bt})dt + \int_{tb}^{tc}(c' + a' \times e^{b't})dt - (c+a) \times (tc-ta)$$

or using the formula:

$$Sin = \int_{ta}^{tb} a \times (e^{-bt}-1)dt + \int_{tb}^{tc} a' \times (e^{-b't}-1)dt$$

As was mentioned above, according to an alternative version of the invention, the step of determining the area Sin of the upstream perturbation region is carried out once and for all for a calibrated variation in the characteristic of the dialysis liquid, the parameters (magnitude, duration and profile) of which are stored in memory in the control unit 30. The area Sin may be calculated from measured values of the conductivity or it may be calculated from set values defining the perturbation. When the area Sin of the upstream perturbation region has been determined (either prior to a particular treatment session or at the start of a particular treatment session), this quantity is stored in memory in the control unit 30 and, every time the method is subsequently implemented it is this quantity that is used.

3—Determination of a quantity indicative of the variation in the characteristic downstream of the haemodialyser 1, as it appears, deformed by the exchanges having taken place in the haemodialyser 1.

In accordance with the invention, the quantity chosen is the area Sout of a region called the "downstream perturbation region" which is defined as follows.

Since the conductivity of the dialysis liquid upstream of the haemodialyser 1 is constant (Cd0in), the conductivity of the spent liquid, as measured by the probe 25, either slowly varies exponentially or remains substantially constant (the situation in FIG. 2) depending on whether there is an appreciable difference in conductivity between the blood and the dialysis liquid or whether this difference is zero or almost zero. Thereafter, it will be assumed that the conductivity of the spent liquid remains substantially constant and equal to Cd0out. This value, measured by the probe 25, is stored in memory.

After a variation in the conductivity of the fresh dialysis liquid has been initiated, as explained above, the fourth conductivity probe 25 placed in the discharge line 10 measures the conductivity continuously and the control unit 30 samples a plurality of values of the conductivity Cdjout of the spent dialysis liquid deviating from the initial conductivity Cd0out.

When the conductivity of the spent dialysis liquid has resumed its initial value Cd0out, the control unit 30 calculates the area Sout of the downstream perturbation region which is bounded by:

a baseline consisting of the initial value Cd0out of the conductivity downstream of the haemodialyser 1, corresponding to the nominal value Cd0in of the conductivity upstream of the haemodialyser 1, and a curve representing the variation with respect to time in the conductivity of the spent liquid over the duration of the perturbation t3–t1, this curve being established from the values Cdjout measured by the probe 25 and sampled by the control unit 30.

The calculation of the area of the perturbation region, Sout, may be carried out, for example, using the elementary-area method or using the integration method, which have been described in detail with regard to the calculation of the area Sin of the upstream perturbation region.

If the control unit 30 carries out the calculation using the elementary-area method, the area Sout of the downstream perturbation region is obtained from the formula:

$$Sout = \Delta t \times \sum_{o}^{m} [Cdjout - Cd0out]$$

If the control unit 30 carries out the calculation using the integration method, the area Sout of the downstream perturbation region is obtained from the formula:

$$Sout = \int_{t1}^{t2} q \times (e^{-rt} - 1)dt + \int_{t2}^{t3} q' \times (e^{-r't} - 1)dt$$

the curve representing the variation in the conductivity of the spent dialysis liquid consisting of two exponential portions $E_C$ and $E_D$ of respective equations $$yC = p + q \times e^{-rt}$$

(between t1 and t2) and $$yD = p' + q' \times e^{-r't}$$

(between t2 and t3).

In the foregoing, it was assumed that, for the same value of the conductivity Cd0in upstream of the haemodialyser 1, the conductivity of the spent liquid remains substantially constant. If this conductivity varies appreciably, a baseline is used in the calculations which consists either of an exponential section or of a straight-line section, of positive or negative slope, forming an approximation of this exponential. The equation of this straight-line section may, for example, be determined from a first value Cd1out, measured at a time t1, just before the perturbation, and from a second value Cd2out, measured at a time t3 at which the conductivity upstream of the haemodialyser 1 has resumed the value Cd0in and the perturbation has ceased to produce its effects downstream of the haemodialyser 1.

4—Calculation of a parameter indicative of the effectiveness of the treatment administered.

In accordance with the invention, the parameter indicative of the effectiveness of the treatment is calculated by the control unit 30 from the area Sin of the upstream perturbation region and of the area Sout of the downstream perturbation region.

When the characteristic subjected to variation is the concentration in the dialysis liquid of a substance present in the dialysis liquid and in the blood, such as sodium, the control unit calculates the dialysance D of the haemodialyser for this substance by means of the formula:

D=(Qd+Quf)×(1−Sout/Sin)

where Qd is the flow rate of the treatment liquid and Quf is the ultrafiltration flow rate.

The simultaneous implementation, in several repeats, of the method according to the invention and of the method described in the document EP 0,658,352 mentioned above, which makes it possible in particular to calculate the dialysance D, has enabled the great reliability of the method according to the invention to be verified.

The control unit 30 can then calculate the concentration Cbin of sodium in the patient's blood upstream of the haemodialyser by means of the formula:

$$Cbin = \frac{(Cd0in \times Sout/Sin + Cd0out)}{(1 - Sout/Sin)}$$

When the characteristic subjected to variation is the concentration in the dialysis liquid of a substance present in the blood and absent from the dialysis liquid, such as urea, the control unit calculates the clearance K of the haemodialyser for this substance by means of the formula:

K=(Qd+Quf)×(1−Sout/Sin)

where Qd is the flow rate of the treatment liquid and Quf is the ultrafiltration flow rate.

The control unit 30 may then also calculate the concentration Cbin of the urea in the patient's blood upstream of the haemodialyser by means of the formula:

$$Cbin = \frac{Cd0out}{(1 - Sout/Sin)}$$

EXAMPLE

Figure 3:
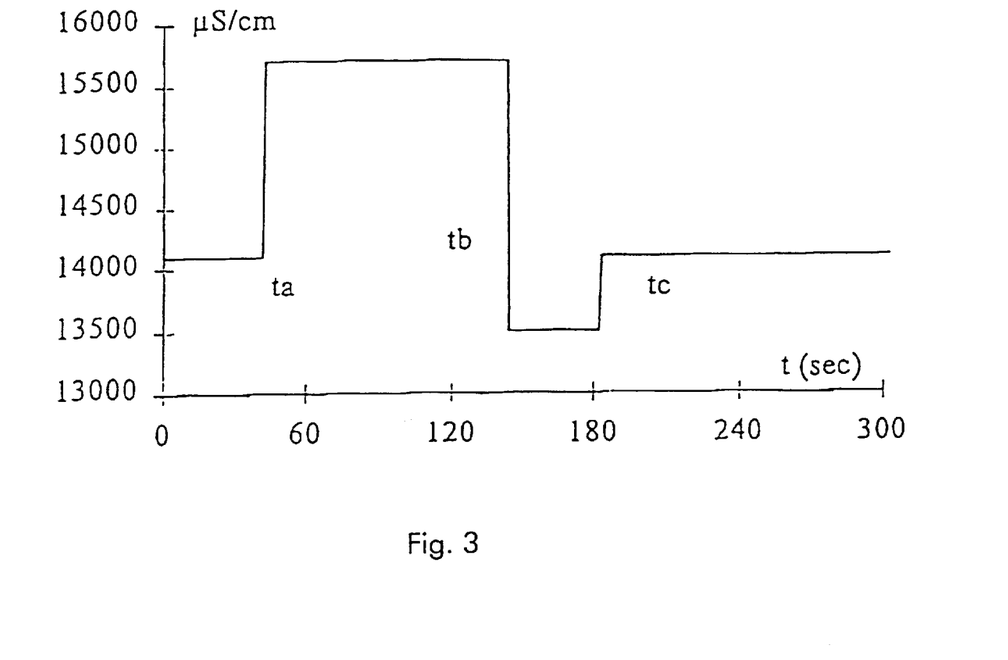
FIG. 3 is a diagram showing an example of conductivity set values for a dialysis liquid, the set values being suitable for implementing the invention.

FIG. 3 shows the set values which have been input into the control unit 30 in order to control the conductivity of the dialysis liquid to a nominal treatment value and to vary the conductivity, at predetermined time intervals or on request, in order to cause a perturbation making it possible to determine the effectiveness of the dialysis session using the method explained above.

The nominal set value was fixed at 14.1 mS/cm. The programmed perturbation comprises a conductivity step of +1.6 mS/cm for 100 s followed by a counter-step of −0.6 mS/cm for 38 s with respect to the nominal set value.

A dialysis treatment was administered to a patient, by means of the system shown in FIG. 1, equipped with an AN69 lanar-membrane dialyser of the CRYSTAL 4000 type, manufactured by the company HOSPAL INDUSTRIE, Meyzieu, France. The various pumps of the system were driven so that the blood flow rate Qb is equal to 200 ml/min, the dialysis liquid flow rate Qd is equal to 500 ml/min and the ultrafiltration flow rate Quf is equal to 20 ml/min.

During the treatment, the initiation of the programmed conductivity perturbation was requested via the control unit 30.

Figure 4:
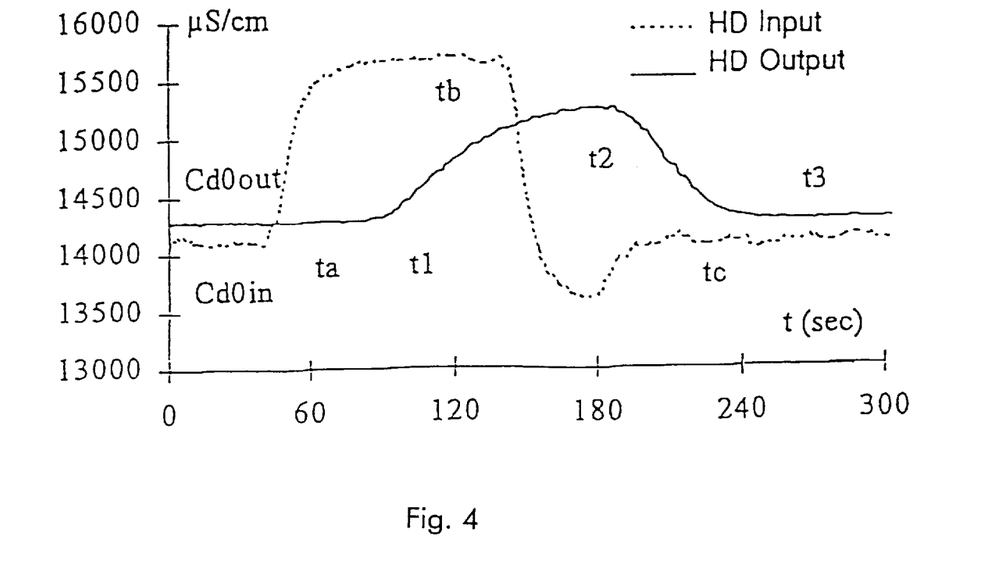
FIG. 4 is a diagram showing the variation in the conductivity of a dialysis liquid upstream and downstream of a dialyser in response to the conductivity set values shown in FIG. 3.

In the graph in FIG. 4, the variation in the conductivity upstream of the dialyser 1, as measured by the probe 23 every 2 seconds (Δt=2 s), is shown by the broken line and the variation in the conductivity downstream of the dialyser, as measured by the probe 25 every 2 seconds, is shown by the solid line. The measured value of the conductivity Cd0in upstream of the dialyser, before and after the perturbation, is equal to 14.113 mS/cm and the measured value of the conductivity Cd0out downstream of the dialyser, before and after the perturbation, is equal to 14.28 mS/cm. In other words, in normal operation, transfer of ionized substances from the blood into the dialysis liquid takes place in the dialyser. The duration tc−ta of the perturbation upstream of the exchanger is equal to 185 s and the duration of the perturbation t3−t1 downstream of the exchanger is equal to 168 s. The area (Sin) of the upstream perturbation region, calculated using the areas method, is equal to:

$$Sin = \Delta t \times \sum_{t=39}^{t=219} [Cdiin - Cd0in]$$

$$= 2 \times \sum_{t=39}^{t=219} [Cdiin - 14,113]$$

$$= 174,45 \text{ mS/cm} \times \text{s}$$

The area (Sout) of the downstream perturbation region, calculated using the areas method, is equal to:

$$Sout = \Delta t \times \sum_{t=85}^{t=238} [Cdjout - Cd0out]$$

$$= 2 \times \sum_{t=85}^{t=238} [Cdjout - 14,281]$$

$$= 114,984 \text{ mS/cm} \times \text{s}$$

The dialysance D of the system is equal to:

D=(Qd+Quf)×(1−Sout/Sin)=177 ml/mil

It will be noted that the patient has been exposed to a dialysis is liquid having a conductivity different from the nominal conductivity only for a very short time (168 seconds, which should be compared with the four hours that a standard dialysis session lasts). It will also be noted that the time needed to determine the dialysance D of the dialysis system, which is approximately equal to the time t3−ta needed to take the measurements, is also very short, i.e. 216 seconds, so that the dialysance D may, if deemed necessary, be determined several times per hour.

The invention is not limited to the illustrative embodiments which have just been described, and variants thereof are possible.

What is claimed is:

1. Method of determining a parameter indicative of the effectiveness of an extracorporeal blood treatment, the parameter being chosen from the group consisting of D, K, Kt/v, Cbin, the method comprising:

flowing blood through a first compartment of a membrane exchanger;

flowing treatment liquid through a second compartment of a membrane exchanger, the second compartment having an inlet connected to an upstream flow path and an outlet connected to downstream flow path;

controlling contents of the upstream flow path to cause an initial substantially constant conductivity value (Cd) in the upstream flow path;

measuring and storing in memory, data sufficient to define a downstream conductivity baseline;

purposefully inducing a conductivity perturbation in the second compartment by varying the conductivity value (Cd) in the upstream flow path for a discrete time period, after which discrete time period the upstream conductivity value is stabilized at the substantially constant conductivity value (Cd);

measuring and storing in memory, during the perturbation, a plurality of downstream perturbation conductivity values defining a downstream curve;

calculating with respect to the downstream baseline, an area bounded by the downstream curve; and calculating, as a function of both the area bounded by the downstream curve and a known area associated with a corresponding upstream curve, the parameter indicative of the effectiveness of a treatment.

2. Method according to claim 1, wherein the perturbation is caused by setting conductivity valve (Cd), over a defined time interval, to a defined set value above or below a nominal value (Cd0in).

3. Method according to claim 1, wherein the perturbation is caused by setting the conductivity valve (Cd), over a first defined time interval, to a first defined set value above (or below) a nominal value (Cd0in), and setting the conductivity valve (Cd, over a second time interval, to a second set value below (or above) the nominal value (Cd0in).

4. Method according to claim 3, further comprising, choosing a duration of the second time interval as well as an absolute value of the second set value so that Cd resumes an initial value (Cd0out) downstream of the exchanger in a minimum amount of time.

5. Method according to one of claims 1 and 2 to 4, further comprising, prior to calculating the parameter indicative of the effectiveness of the extracorporeal treatment, determining the area associated with the upstream curve.

6. Method according to claim 5, further comprising prior to determining the area associated with the upstream curve, measuring a plurality of values adopted by Cd of the treatment liquid upstream of the exchanger during a time period tc–ta.

7. Method according to one of claims 1 and 2 to 4, further comprising, prior to varying the value of Cd:

giving the parameters of the perturbation a defined value, so that the area associated with the upstream curve is constant when predetermined parameters of the perturbation are compiled with;

determining and storing in memory the area associated with the upstream curve for a perturbation having the defined parameters.

8. Method according to claim 1, further comprising determining the area associated with the upstream (or downstream) curve by:

determining an equation for the curve representing a variation, as a function of time, in the measured values of Cd upstream (or downstream) of the exchanger;

calculating an integral of the equation between a start and an end of the variation in the value of Cd; and subtracting from the integral of the equation an area equal to a product of a duration of the perturbation and a nominal value of Cd.

9. Method according to claim 1, wherein the area bounded by at least one of the upstream curve and the downstream curve is determined by:

measuring a value of Cd at time intervals $\Delta t$ throughout a duration of the perturbation;

calculating a series of elementary areas by multiplying each measured value, decreased by a nominal value (Cd0in) (or by the initial value Cd0out) of Cd, by the time interval $\Delta t$; and summing the elementary areas.

10. Method according to claim 1, wherein the conductivity value (Cd) is varied during the perturbation by varying the concentration in the treatment liquid of a substance present in both the treatment liquid and the blood, and in that the dialysance D of the exchanger for the substance is calculated by means of the formula:

$$D = (Qd + Quf) \times (1 - Sout/Sin)$$

where Qd is a flow rate of the treatment liquid and Quf is an ultrafiltration flow rate.

11. Method according to claim 10, characterized in that the substance is sodium.

12. Method according to claim 1, wherein the conductivity value (Cd) is varied during the perturbation by varying the concentration in the treatment liquid of a substance present in the treatment liquid and in the blood and in that a concentration Cbin of the substance in the patient's blood upstream of the exchanger is calculated by means of the formula:

$$Cbin = \frac{(Cd0in \times Sout/Sin + Cd0out)}{(1 - Sout/Sin)}.$$

13. Method according to claim 10 or 12, wherein the perturbation is caused by modifying a discharge rate of a pump associated with a treatment-liquid generator in which a concentrated solution is mixed with water or with a dilute solution, in order to prepare the treatment liquid.

14. Method according to claim 1, wherein the conductivity value (Cd) is varied during the perturbation by varying the concentration in the treatment liquid of a substance present in the blood and absent from the treatment liquid, and in that the clearance K of the exchanger for the substance is calculated by means of the formula:

$$K = (Qd + Quf) \times (1 - Sout/Sin)$$

where Qd is the flow rate of the treatment liquid and Quf is an ultrafiltration flow rate.

15. Method according to claim 14, characterized in that the substance is urea.

16. Method according to claim 1, wherein the conductivity value (Cd) is varied during the perturbation by varying the concentration in the treatment liquid of a substance present in the blood and absent from the treatment liquid and in that a concentration Cbin of the substance in the patient's blood upstream of the exchanger is calculated by means of the formula:

$$Cbin = \frac{Cd0out}{(1 - Sout/Sin)}.$$

17. Method according to one of claims 10, 11, 12 or 16, characterized in that the perturbation is caused by injecting a volume of a liquid containing the substance into the treatment liquid upstream of the exchanger.

18. Method according to claim 17, characterized in that a defined volume of the substance is injected into the treatment liquid so that the area associated with the upstream curve can be predetermined.

19. Method of claim 1, wherein the known area is calculated from measurements and stored in memory.

20. Method of claim 1, further including measuring and storing in memory an upstream baseline conductivity value, and measuring and storing in memory, during the upstream baseline conductivity value punctuated by a curve defined by the stored upstream perturbation conductivity values area used to obtain the known area.

* * * * *

UNITED STATES PATENT AND TRADEMARK OFFICE
CERTIFICATE OF CORRECTION

PATENT NO.    : 6,110,384

DATED:        August 29, 2000

INVENTORS:    Nicolas GOUX, Jan STERNBY

It is hereby certified that errors appear in the above-identified patent and that said Letters Patent is hereby corrected as shown below:

Claim 3, col. 13, line 34, change "(Cd," to -- (Cd),--.

Claim 7, col. 23, line 55, change "compiled" to --complied--.

Claim 17, col. 15, line 5, change "claims 10, 11, 12 or 16" to --claims 10, 12, 14, or 16--.

Claim 20, col. 16, line 6, after "during the" insert --perturbation, a plurality of upsteam perturbation conductivity values, wherein the stored--.

Claim 20, col. 16, line 8, change "area" to --are--.

Signed and Sealed this

Seventeenth Day of April, 2001

*Attest:*

NICHOLAS P. GODICI

*Attesting Officer*    Acting Director of the United States Patent and Trademark Office